United States Patent
Takayama et al.

(10) Patent No.: US 12,279,358 B2
(45) Date of Patent: Apr. 15, 2025

(54) PARTICLE BEAM ACCELERATOR, METHOD FOR OPERATING PARTICLE BEAM ACCELERATOR, AND PARTICLE BEAM THERAPY APPARATUS

(71) Applicants: KABUSHIKI KAISHA TOSHIBA, Tokyo (JP); TOSHIBA ENERGY SYSTEMS & SOLUTIONS CORPORATION, Kawasaki (JP)

(72) Inventors: Shigeki Takayama, Yokohama (JP); Shinya Matsuda, Kamakura (JP); Takayuki Sako, Yamato (JP); Tomofumi Orikasa, Yokohama (JP)

(73) Assignees: KABUSHIKI KAISHA TOSHIBA, Tokyo (JP); TOSHIBA ENERGY SYSTEMS & SOLUTIONS CORPORATION, Kawasaki (JP)

( * ) Notice: Subject to any disclaimer, the term of this patent is extended or adjusted under 35 U.S.C. 154(b) by 249 days.

(21) Appl. No.: 18/297,861

(22) Filed: Apr. 10, 2023

(65) Prior Publication Data
US 2023/0262869 A1   Aug. 17, 2023

Related U.S. Application Data (63) Continuation of application No. PCT/JP2021/038469, filed on Oct. 18, 2021.

(30) Foreign Application Priority Data

Dec. 9, 2020   (JP) ................................ 2020-203944

(51) Int. Cl.
*H05H 7/04* (2006.01)
*A61N 5/10* (2006.01)
(Continued)

(52) U.S. Cl.
CPC ............. *H05H 7/04* (2013.01); *A61N 5/1078* (2013.01); *H05H 7/08* (2013.01); *H05H 7/10* (2013.01);
(Continued)

(58) Field of Classification Search
None
See application file for complete search history.

(56) References Cited

U.S. PATENT DOCUMENTS 5,218,505 A     6/1993  Kubo et al.
5,455,292 A  *  10/1995  Kakegawa ............. C08K 5/523
                                                        524/127
(Continued)

FOREIGN PATENT DOCUMENTS

JP      59-41181 A    3/1984
JP       3-40409 A    2/1991
(Continued)

OTHER PUBLICATIONS

International Search Report issued Dec. 14, 2021 in PCT/JP2021/038469 filed on Oct. 18, 2021, citing documents 2, 17-22 therein, 2 pages.

*Primary Examiner* — Srinivas Sathiraju
(74) *Attorney, Agent, or Firm* — Oblon, McClelland, Maier & Neustadt, L.L.P.

(57) ABSTRACT

According to one embodiment, a particle beam accelerator comprising: an injection unit configured to inject a particle beam; a guiding unit configured to guide the particle beam to a trajectory; an acceleration unit configured to accelerate the particle beam circulating on the trajectory; an emission unit configured to output the particle beam; a particle beam blocking unit configured to block the particle beam on the trajectory; a control unit configured to control the injection unit, the guiding unit, the acceleration unit, the emission unit, and the particle beam blocking unit, wherein: the
(Continued)

guiding unit includes a superconducting electromagnet and a superconducting electromagnet interrupter configured to interrupt the superconducting electromagnet, the control unit is configured to change a starting sequence of the particle beam blocking unit and the superconducting electromagnet interrupter depending on at least an operating state of the emission unit, when an abnormality occurs in the superconducting electromagnet.

4 Claims, 5 Drawing Sheets

(51) Int. Cl.
  *H05H 7/08* (2006.01)
  *H05H 7/10* (2006.01)
  *H05H 13/04* (2006.01)
(52) U.S. Cl.
  CPC ..... *H05H 13/04* (2013.01); *A61N 2005/1087* (2013.01); *H05H 2007/043* (2013.01); *H05H 2007/046* (2013.01); *H05H 2277/11* (2013.01)

(56) References Cited

U.S. PATENT DOCUMENTS

| | | | | |
|---|---|---|---|---|
| 5,871,075 | A * | 2/1999 | Takayama | G07D 3/00 194/318 |
| 10,886,041 | B2 * | 1/2021 | Tosaka | H10N 60/203 |
| 2002/0016043 | A1 * | 2/2002 | Hosono | G05F 1/56 438/297 |
| 2002/0147274 | A1 * | 10/2002 | Sasagawa | C08F 297/04 525/98 |
| 2003/0125475 | A1 * | 7/2003 | Sasagawa | C08C 19/02 525/333.1 |
| 2003/0162908 | A1 * | 8/2003 | Sasagawa | C08L 23/10 525/331.9 |
| 2004/0039128 | A1 * | 2/2004 | Sasagawa | C08F 8/04 525/333.3 |
| 2004/0157994 | A1 * | 8/2004 | Kubo | C09J 7/38 525/88 |
| 2004/0176514 | A1 * | 9/2004 | Kubo | C08L 53/005 524/437 |
| 2005/0119414 | A1 * | 6/2005 | Sasagawa | C08F 8/00 525/242 |
| 2005/0171276 | A1 * | 8/2005 | Matsuda | C09J 151/04 524/572 |
| 2005/0234193 | A1 * | 10/2005 | Sasagawa | C08F 8/04 525/88 |
| 2015/0380138 | A1 * | 12/2015 | Takayama | H01F 6/06 505/211 |
| 2016/0005538 | A1 * | 1/2016 | Koyanagi | H01F 41/048 505/433 |
| 2016/0240284 | A1 * | 8/2016 | Tosaka | H10N 60/80 |
| 2017/0229281 | A1 * | 8/2017 | Furukawa | G21K 5/04 |
| 2018/0166180 | A1 * | 6/2018 | Takayama | G21K 1/00 |
| 2018/0214715 | A1 * | 8/2018 | Takayama | A61N 5/1042 |
| 2019/0255357 | A1 * | 8/2019 | Takayama | A61N 2/06 |
| 2020/0001119 | A1 * | 1/2020 | Nonaka | H05H 7/02 |
| 2023/0247753 | A1 * | 8/2023 | Takayama | A61N 5/10 315/503 |
| 2023/0262869 | A1 * | 8/2023 | Takayama | H05H 7/10 315/503 |
| 2023/0360831 | A1 * | 11/2023 | Takayama | H05H 7/04 |
| 2024/0096534 | A1 * | 3/2024 | Takayama | H05H 7/04 |

FOREIGN PATENT DOCUMENTS

| | | |
|---|---|---|
| JP | 2015-159060 A | 9/2015 |
| JP | 2017-33978 A | 2/2017 |
| JP | 2017-162896 A | 9/2017 |
| JP | 2018-149179 A | 9/2018 |
| JP | 2019-88414 A | 6/2019 |
| JP | 2019-141245 A | 8/2019 |

* cited by examiner

PARTICLE BEAM ACCELERATOR, METHOD FOR OPERATING PARTICLE BEAM ACCELERATOR, AND PARTICLE BEAM THERAPY APPARATUS

CROSS-REFERENCE TO RELATED APPLICATIONS

This application is a Continuation Application of No. PCT/JP2021/038469, filed on Oct. 18, 2021, and the PCT application is based upon and claims the benefit of priority from Japanese Patent Application No. 2020-203944, filed on Dec. 9, 2020, the entire contents of which are incorporated herein by reference.

TECHNICAL FIELD

Embodiments of the present invention relate to a technique for particle beam acceleration

BACKGROUND

In recent years, attention has been focused on a particle beam therapy technique in which a patient's diseased tissue such as cancer is irradiated with a particle beam of carbon ions for treatment. Since this particle beam therapy technique can pinpoint and kill only the diseased tissue without damaging normal tissues, the burden on the patient is less than surgery or medication treatment, and earlier return to society after the treatment can also be expected.

In order to treat cancer cells deep inside the body, it is necessary to accelerate the particle beam. In general, particle beam accelerators configured to accelerate the particle beam are broadly classified into two types. One of the two types is a linear accelerator in which a high-frequency acceleration cavity is arranged in a straight line, and the other type is a circular accelerator in which a deflectors configured to bend the trajectory of a particle beam are arranged approximately circularly and a high-frequency acceleration cavity is disposed in part of this circular trajectory. In particular, for heavy particles such as carbons and protons, it is common to adopt the method in which a linear accelerator is used for acceleration in the low energy band immediately after generation of the particle beam and a circular accelerator is used for acceleration in the high energy band.

The circular accelerator configured to circulate and accelerate the particle beam is configured by sequentially arranging: a focusing/defocusing apparatus configured to control the shape of the particle beam; a deflector configured to bend the trajectory of the particle beam; and a steering electromagnet configured to correct deviation of the trajectory of the particle beam. In this circular accelerator, when mass or energy of the circulating particles increases, magnetic rigidity (i.e., difficulty of bending due to the magnetic field) increases and thus the trajectory radius of the particle beam increases. As a result, the entirety of the apparatus including the circular accelerator becomes large in size. As the size of the apparatus increases, the incidental facilities in the building also increase in size, which makes it difficult to introduce this apparatus in a place where the installation range is limited, such as in an urban site.

In order to suppress increase in size of the circular accelerator, it is necessary to increase the magnetic field strength to be generated by the deflector. Ina general deflector, though influence of magnetic saturation of its iron core makes it difficult to generate a magnetic field exceeding 1.5 T, application of superconducting technology to the deflector enables enhancement in magnetic field strength and thus enables reduction in size of the circular accelerator. However, if an abnormality such as quenching occurs in the superconducting electromagnet constituting the deflector of the circular accelerator for the particle beam therapy apparatus, there is a possibility that the particle beam is erroneously radiated to the patient. When blocking of the particle beam is given priority over interruption of the superconducting electromagnet in order to avoid the above-described risk of erroneous irradiation, the recovery time of the superconducting electromagnet becomes longer.

PRIOR ART DOCUMENT

Patent Document

[Patent Document 1] JP 2019-141245 A
[Patent Document 2] JP 2015-159060 A
[Patent Document 3] JP 2017-033978 A

SUMMARY

Problems to be Solved by Invention

An object of the present invention is to: enable reduction of the risk of erroneous irradiation of the particle beam by appropriately keeping the particle beam in a predetermined trajectory in a particle beam accelerator; and shorten the recovery time of a superconducting electromagnet constituting the particle beam accelerator.

DETAILED DESCRIPTION

In one embodiment of the present invention, a particle beam accelerator comprising: an injection unit configured to inject a particle beam; a guiding unit configured to guide the particle beam to a trajectory; an acceleration unit configured to accelerate the particle beam circulating on the trajectory; an emission unit configured to output the particle beam; a particle beam blocking unit configured to block the particle beam on the trajectory; and a control unit configured to control the injection unit, the guiding unit, the acceleration unit, the emission unit, and the particle beam blocking unit, wherein: the guiding unit includes a superconducting electromagnet and a superconducting electromagnet interrupter configured to interrupt the superconducting electromagnet, and the control unit is configured to change a starting sequence of the particle beam blocking unit and the superconducting electromagnet interrupter depending on at least an operating state of the emission unit, when an abnormality occurs in the superconducting electromagnet.

Hereinbelow, embodiments of a particle beam accelerator, a method for operating particle beam accelerator, and a particle beam therapy apparatus will be described in detail by referring to the accompanying drawings.

Figure 1:
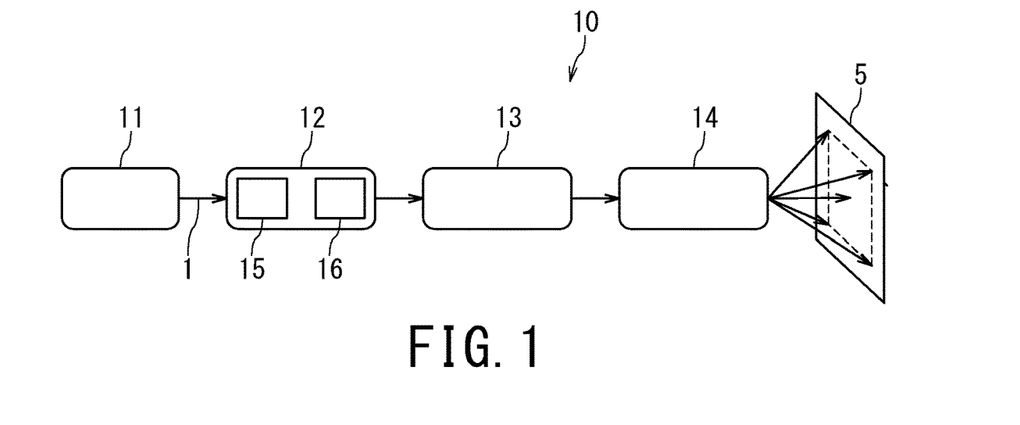
FIG. 1 is a block diagram illustrating a charged particle beam therapy apparatus.

As shown in FIG. 1, a charged particle beam therapy apparatus as a particle beam therapy apparatus according to the present embodiment is an apparatus that uses charged particles (for example, negative pions, protons, helium ions, carbon ions, neon ions, silicon ions, and argon ions) as a charged particle beam source for therapeutic irradiation. This charged particle beam therapy apparatus 10 includes: a particle beam generator 11; a particle beam accelerator 12; a particle beam transport apparatus 13; and a particle beam irradiator 14. This charged particle beam therapy apparatus 10 irradiates a lesion site 5 of a patient as an irradiation target with a charged particle beam 1. The charged particle beam 1 is used to treat the lesion site 5.

The particle beam generator 11 is an apparatus that generates the charged particle beam 1 and is, for example, an apparatus that extracts ions and the like generated by using an electromagnetic field or a laser.

The particle beam accelerator 12 is an apparatus that accelerates the charged particle beam 1 to a predetermined energy. As one aspect, FIG. 1 illustrates a configuration provided with two-stage accelerators that is composed of a front-stage accelerator 15 and a rear-stage accelerator 16. Aspects of the front-stage accelerator 15 include a linear accelerator such as a drift tube linac (DTL) and a radio-frequency quadrupole linear accelerator (RFQ). Aspects of the rear-stage accelerator 16 include a circular accelerator such as a synchrotron and a cyclotron.

The particle beam accelerator 12 includes: a vacuum duct 20 (piping) configured to keep the passage space of charged particle beam 1 vacuum and airtight; a high-frequency acceleration cavity 24 configured to accelerate the charged particle beam 1 by an electric field; deflectors 21 configured as dipole electromagnets to stably guide the charged particle beam 1; and focusing/defocusing apparatuses 22 configured as quadrupole electromagnets; and a controller 30 configured to control each of these components.

The particle beam transport apparatus 13 is a system that transports the charged particle beam 1 accelerated by the particle beam accelerator 12 to the particle beam irradiator 14. The particle beam transport apparatus 13 includes: a vacuum duct; deflectors; focusing/defocusing apparatuses; and a controller configured to control these components.

The particle beam irradiator 14 is installed at the downstream of the particle beam transport apparatus 13. In order to accurately irradiate the irradiation point having been set at the lesion site 5 of the patient with the charged particle beam 1 that has passed through this particle beam transport apparatus 13 and has specific energy, the particle beam irradiator 14 adjusts the trajectory 3 of the charged particle beam 1 and further monitors the irradiation position and irradiation dose of the charged particle beam 1 at the lesion site 5.

Figure 2:
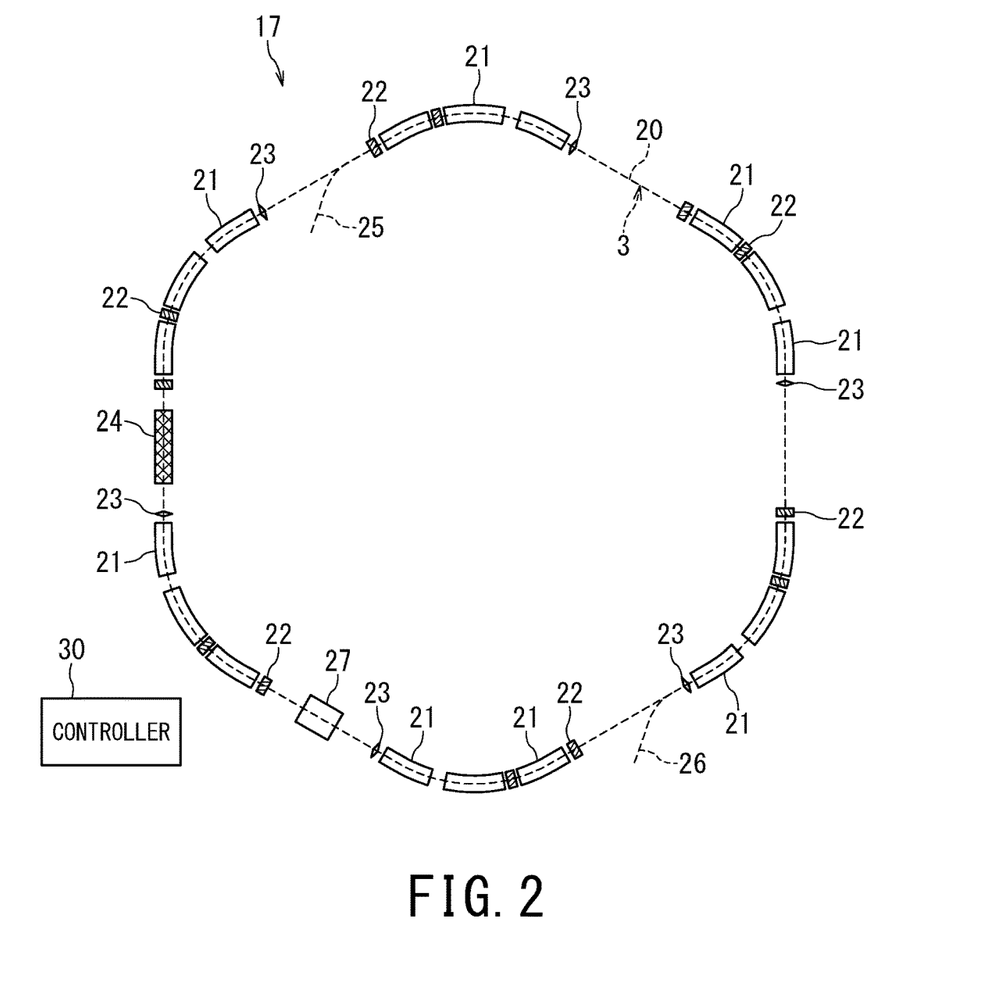
FIG. 2 is a plan view illustrating a superconducting synchrotron.

FIG. 2 shows a superconducting synchrotron 17 as the rear-stage accelerator 16 of the particle beam accelerator 12 described above. This superconducting synchrotron 17 is an apparatus that accelerates the charged particle beam 1 while circulating the charged particle beam 1. The superconducting synchrotron 17 is configured by arranging: a plurality of deflectors 21; a plurality of focusing/defocusing apparatuses 22; a plurality of hexapole electromagnets 23; a high-frequency acceleration cavity 24; a beam injector 25; a beam emitter 26; and a charged particle beam blocker 27, on the outer diameter side of the ring-shaped vacuum duct 20. The superconducting synchrotron 17 further includes a controller 30.

The vacuum duct 20 is piping that keeps the passage space of the charged particle beam 1 vacuum and airtight. On its axis, a predetermined trajectory 3 through which the charged particle beam 1 passes is formed.

Each deflector 21 is composed of a dipole electromagnet, and circulates the charged particle beam 1 along the predetermined trajectory 3 by the magnetic field to be generated. Each focusing/defocusing apparatus 22 is composed of a quadrupole electromagnet, and focuses or defocuses the charged particle beam 1 circulating on the predetermined trajectory 3 by the magnetic field to be generated. Thus, the deflectors 21 and the focusing/defocusing apparatuses 22 function as a guiding unit that stably guides the charged particle beam 1 along the predetermined trajectory 3.

The high-frequency acceleration cavity 24 functions as an acceleration unit configured to accelerate the charged particle beam 1 circulating along the predetermined trajectory 3 in the vacuum duct 20 by an electric field that is generated by applying a high-frequency voltage. In addition, the beam injector 25 functions as an injection unit configured to inject the charged particle beam 1 generated by the particle beam generator 11 into the superconducting synchrotron 17. Further, the beam emitter 26 functions as an emission unit configured to emit the charged particle beam 1 accelerated by the superconducting synchrotron 17 to the particle beam transport apparatus 13.

The charged particle beam blocker 27 functions as a particle beam blocking unit configured to urgently block the charged particle beam 1 circulating on the predetermined trajectory 3 inside the vacuum duct 20. This blocking by the charged particle beam blocker 27 is, specifically, blocking of the charged particle beam 1 by closing a gate (not shown), blocking of the charged particle beam 1 by a bump electromagnet (not shown) configured to deviate the charged particle beam 1 into a disposal orbit, or the like. In addition, the controller 30 functions as a control unit configured to control the deflectors 21, the focusing/defocusing apparatuses 22, the hexapole electromagnets 23, the high-frequency acceleration cavity 24, the beam injector 25, the beam emitter 26, and the charged particle beam blocker 27 described above.

Each of the above-described deflectors 21 and the focusing/defocusing apparatuses 22 includes a normal-conducting electromagnet in general. In the present embodiment, either or both of each deflector 21 and each focusing/defocusing apparatus 22 is configured as a superconducting electromagnet apparatus 31 that includes a superconducting electromagnet 32 shown in FIG. 3. This superconducting electromagnet apparatus 31 is configured by: connecting the superconducting electromagnet 32, an excitation power supply 33, and a circuit breaker 34 in series; and connecting a protective resistance 35 to the superconducting electromagnet 32 in parallel.

Figure 3:
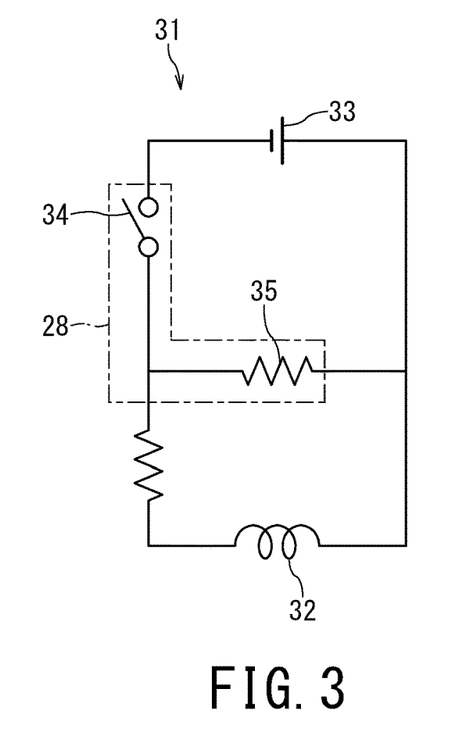
FIG. 3 is an electric circuit diagram illustrating a superconducting electromagnet apparatus.

When an abnormality such as quenching occurs in the superconducting electromagnet 32, a quench detector (not shown) outputs a quench signal and thereby the circuit breaker 34 opens. This opening operation of the circuit breaker 34 forms a closed circuit in which the superconducting electromagnet 32 and the protective resistance 35 are connected in series. As a result, the energy stored in the superconducting electromagnet 32 is consumed by the protective resistance 35 and the superconducting electromagnet 32 is disconnected. Thus, the above-described circuit breaker 34 and the protective resistance 35 constitute the superconducting electromagnet interrupter 28 configured to interrupt the superconducting electromagnet 32.

Figure 5:
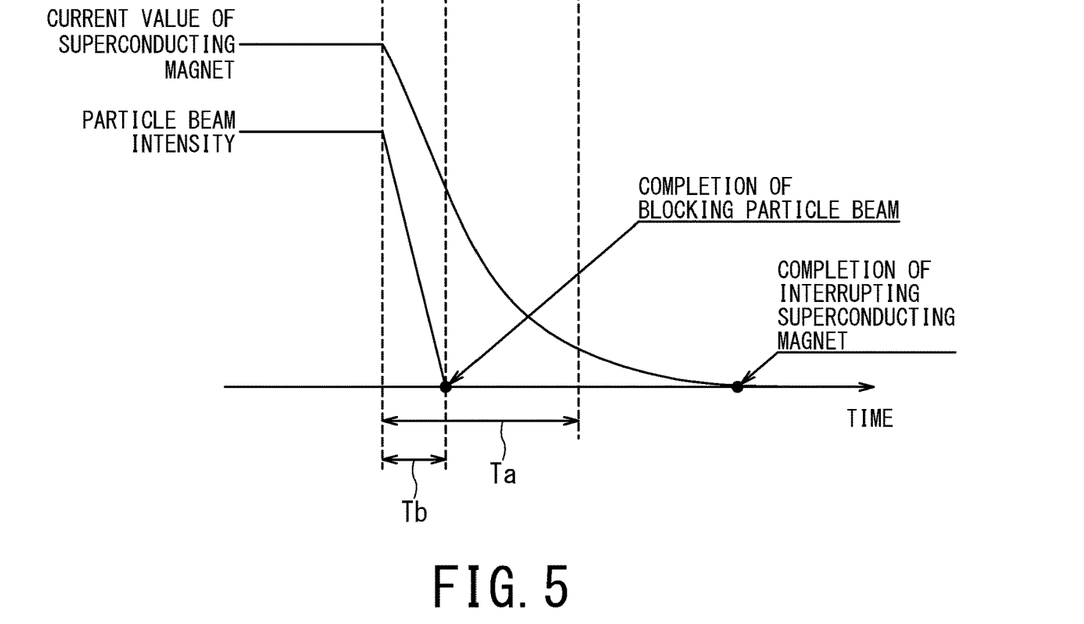
FIG. 5 is a timing chart illustrating change in current value of a superconducting electromagnet and change in particle beam intensity in the case of simultaneously activating both a superconducting electromagnet interrupter and a charged particle beam blocker.

In either or both the focusing/defocusing apparatuses 22 and the deflectors 21 configured as the superconducting electromagnet apparatuses 31, an abnormality such as quenching may occur in the superconducting electromagnet 32. When the charged particle beam blocker 27 (FIG. 2) and the superconducting electromagnet interrupter 28 (FIG. 3) are activated at the same time, it causes a problem. For example, as shown in FIG. 5, it is assumed that both: blocking of the charged particle beam 1 by the charged particle beam blocker 27; and interruption of the superconducting electromagnet 32 by the superconducting electromagnet interrupter 28 are simultaneously started. When the current value of the superconducting electromagnet 32 subjected to quenching or the like changes (decreases) before completion of blocking the charged particle beam 1, there is a possibility that the charged particle beam 1 before completion of blocking deviates from the predetermined trajectory 3.

When the charged particle beam 1 deviates largely from the predetermined trajectory 3, the charged particle beam 1 collides with the vacuum duct 20 and is lost. When the charged particle beam 1 deviates slightly from the predetermined trajectory 3, there is a possibility that the charged particle beam 1 reaches the position of the patient so as to be erroneously radiated to an unexpected site of the patient by the particle beam irradiator 14, for example, a site outside the lesion tissue.

Figure 4:
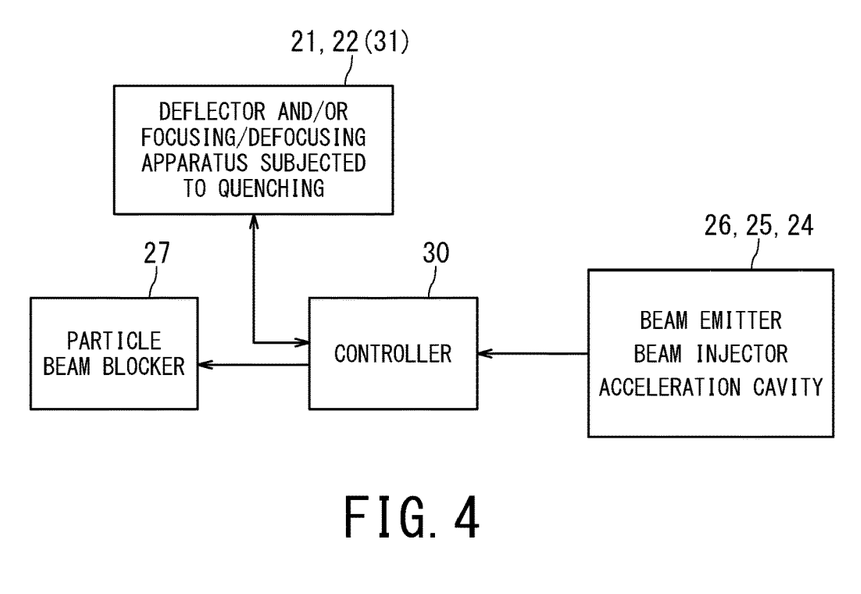
FIG. 4 is a block diagram illustrating a control system in the superconducting synchrotron.

For this reason, as shown in FIG. 4, when the controller 30 of the present embodiment receives the quench signal in response to occurrence of an abnormality such as quenching in the superconducting electromagnet 32 of the superconducting electromagnet apparatus 31 constituting either or both the deflector 21 and the focusing/defocusing apparatus 22, the controller 30 changes a starting sequence of the charged particle beam blocker 27 and the superconducting electromagnet interrupter 28 depending on at least the operating state of the beam emitter 26, for example, depending on the respective operating states of the beam emitter 26, the high-frequency acceleration cavity 24, the beam injector 25, and the like.

Specifically, the controller 30 performs first blocking control. For example, there are times when the beam emitter 26 operates and the charged particle beam 1 is extracted and outputted from the superconducting synchrotron 17. At this time, when an abnormality such as quenching occurs in the superconducting electromagnet 32, first, the charged particle beam blocker 27 is activated and thereby the charged particle beam 1 is blocked. After completion of blocking the charged particle beam 1, the superconducting electromagnet interrupter 28 is activated and thereby the superconducting electromagnet 32 subjected to quenching or the like is disconnected.

Figure 6:
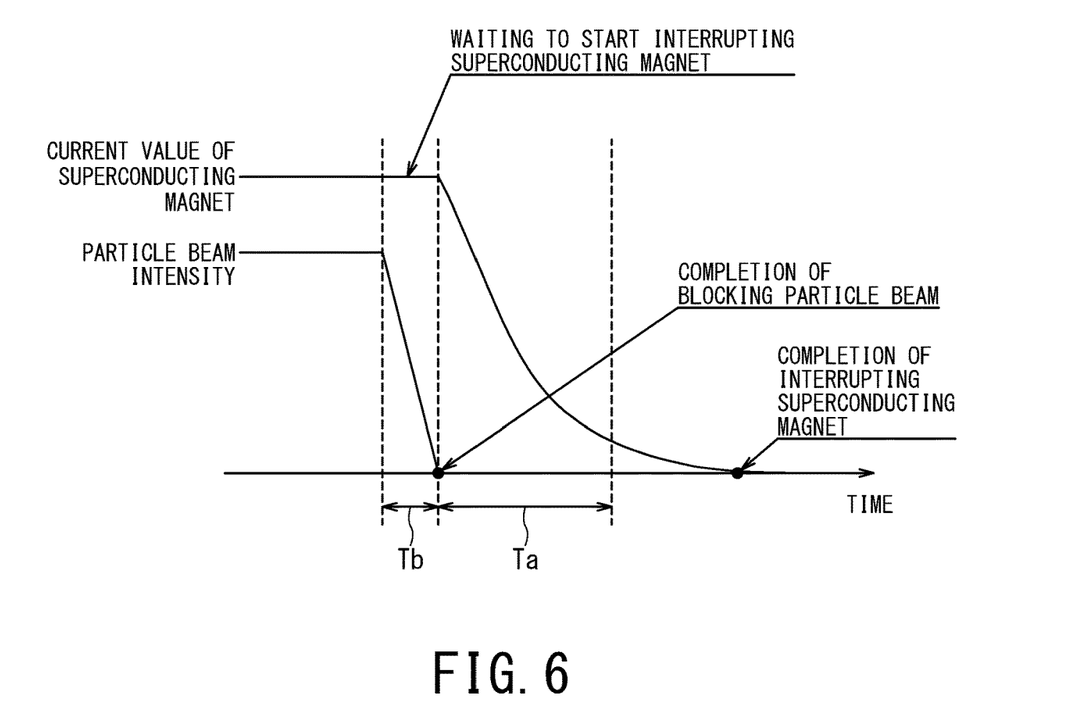
FIG. 6 is a timing chart illustrating change in current value of the superconducting electromagnet and change in particle beam intensity when the superconducting electromagnet interrupter is activated after completion of blocking the charged particle beam by the charged particle beam blocker.

As a result, as shown in FIG. 6, the current value of the superconducting electromagnet 32 subjected to quenching or the like does not decrease and is maintained at an appropriate value during the period from the start of blocking the charged particle beam 1 to its completion, and thus, the charged particle beam 1 is blocked without deviating from the predetermined trajectory 3 in the superconducting synchrotron 17.

As shown in FIG. 3, a resistance value of the protective resistance 35 of the superconducting electromagnet apparatus 31 is set in such a manner that an interruption time constant Ta of the superconducting electromagnet interrupter 28 is longer than a blocking time constant Tb of the charged particle beam blocker 27. The interruption time constant Ta is the time length from the start of interrupting the superconducting electromagnet 32 to its completion. The blocking time constant Tb is the time length from the start of blocking the charged particle beam 1 to its completion.

In other words, the interruption time constant Ta of the superconducting electromagnet interrupter 28 is determined by selecting the resistance value of the protective resistance 35 depending on rise in coil temperature and generated voltage at the time of occurrence of quenching (or the like) in the superconducting electromagnet 32, and is set to approximately ten seconds or less, for example.

Since the blocking of the charged particle beam 1 by charged particle beam blocker 27 is achieved by closing of the gate or deviation of the beam by the bump electromagnet, the blocking time constant Tb of the charged particle beam blocker 27 is set to approximately 100 milliseconds or less. Thus, the interruption time constant Ta of the superconducting electromagnet interrupter 28 is longer than the blocking time constant Tb of the charged particle beam blocker 27, i.e., the blocking time constant Tb of the charged particle beam blocker 27 is set sufficiently shorter than the interruption time constant Ta of the superconducting electromagnet interrupter 28. Hence, generation of large voltage and rise in coil temperature in the superconducting electromagnet 32 subjected to quenching or the like is suppressed as much as possible.

In addition, the controller 30 performs second blocking control. For example, during non-operation of the beam emitter 26, there are times when: the charged particle beam 1 is injected into the superconducting synchrotron 17 by the beam injector 25; the charged particle beam 1 is accelerated by the high-frequency acceleration cavity 24; or the accelerated charged particle beam 1 is kept so as to be accumulated. At this time, when an abnormality such as quenching occurs in the superconducting electromagnet 32, the superconducting electromagnet interrupter 28 is activated simultaneously with the charged particle beam blocker 27. Further, both: interruption of the superconducting electromagnet 32 subjected to quenching or the like by the superconducting electromagnet interrupter 28; and blocking of the charged particle beam 1 by the charged particle beam blocker 27 are executed simultaneously.

In this case, as shown in FIG. 5, the current value of the superconducting electromagnet 32 subjected to quenching or the like decreases before completion of blocking the charged particle beam 1, and thus, the charged particle beam 1 before completion of blocking deviates from the predetermined trajectory 3. For this reason, the charged particle beam 1 is blocked by providing a gate or the like between the superconducting synchrotron 17 and the patient, for example, in the particle beam transport apparatus 13 or in the particle beam irradiator 14. This configuration prevents a situation in which the charged particle beam 1 having deviated from the predetermined trajectory 3 in the superconducting synchrotron 17 is erroneously radiated to an unexpected site of the patient by the particle beam irradiator 14.

Next, on the basis of FIG. 7 and FIG. 8, a description will be given of the blocking control of the charged particle beam blocker 27 and the superconducting electromagnet interrupter 28 by the controller 30, including the action and effect to be passively caused by the operation of the charged particle beam blocker 27 and the superconducting electromagnet interrupter 28.

Figure 7:
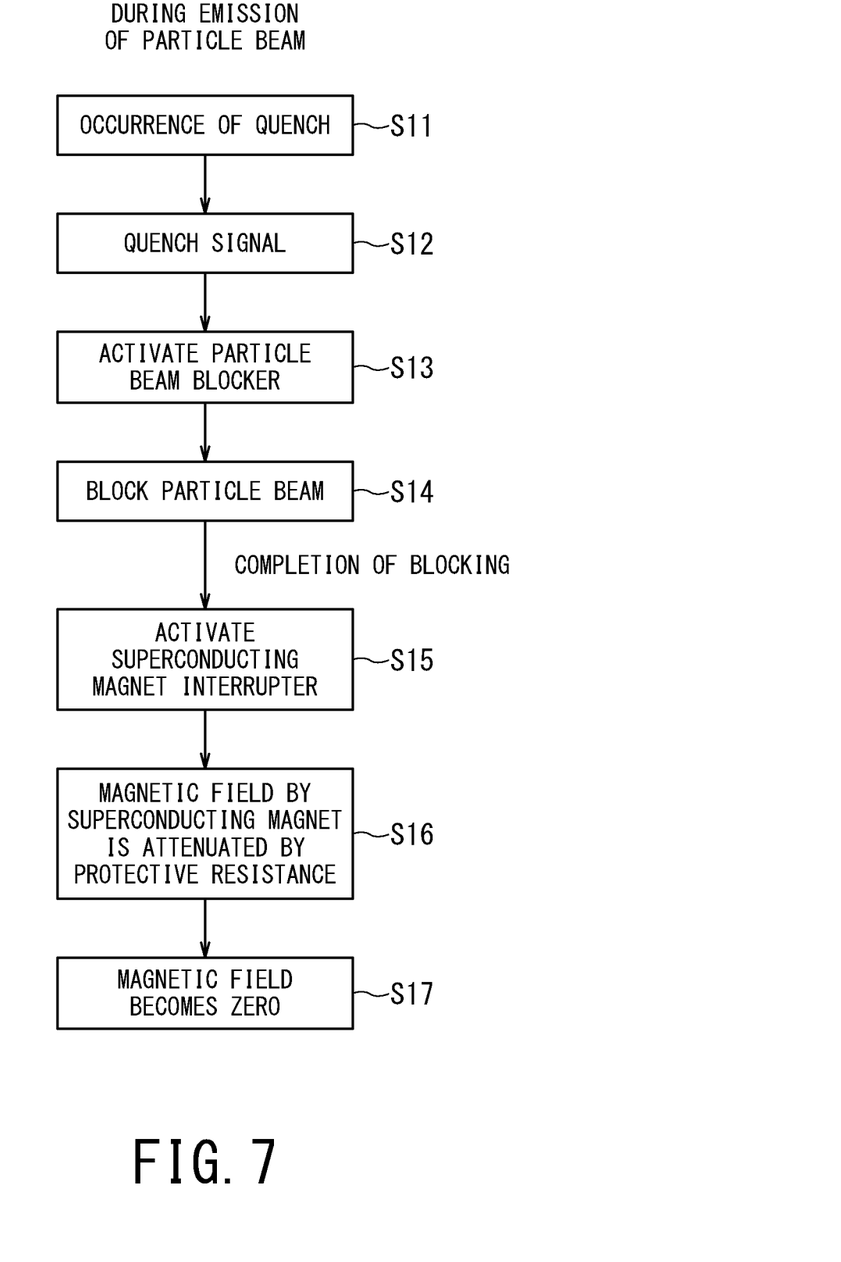
FIG. 7 is a flowchart illustrating a blocking procedure by the charged particle beam blocker and the superconducting electromagnet interrupter during emission of the particle beam.

As shown in FIG. 7, the controller 30 performs the first blocking control. In the first step S11, during operation of the beam emitter 26 in the superconducting synchrotron 17, an abnormality such as quenching occurs in the superconducting electromagnet 32 of the superconducting electromagnet apparatus 31 constituting either or both the deflector 21 and the focusing/defocusing apparatus 22.

In the next step S12, the quench detector (not shown) detects the abnormality such as quenching of the superconducting electromagnet 32 so as to output the quench signal, and then the controller 30 receives the quench signal from the quench detector.

In the next step S13, the controller 30 activates the charged particle beam blocker 27 at the timing of receiving the quench signal from the quench detector.

In the next step S14, the charged particle beam blocker 27 performs blocking of the charged particle beam 1, and the controller 30 waits until completion of blocking the charged particle beam 1.

In the next step S15, the charged particle beam 1 is blocked by the charged particle beam blocker 27, and the controller 30 activates the superconducting electromagnet interrupter 28 at the timing when this blocking is completed.

In the next step S16, due to activation of the superconducting electromagnet interrupter 28, the magnetic field of the superconducting electromagnet 32 subjected to quenching or the like is attenuated by the protective resistance 35.

In the next step S17, interruption of the superconducting electromagnet 32 is completed at the timing when the magnetic field becomes zero.

Figure 8:
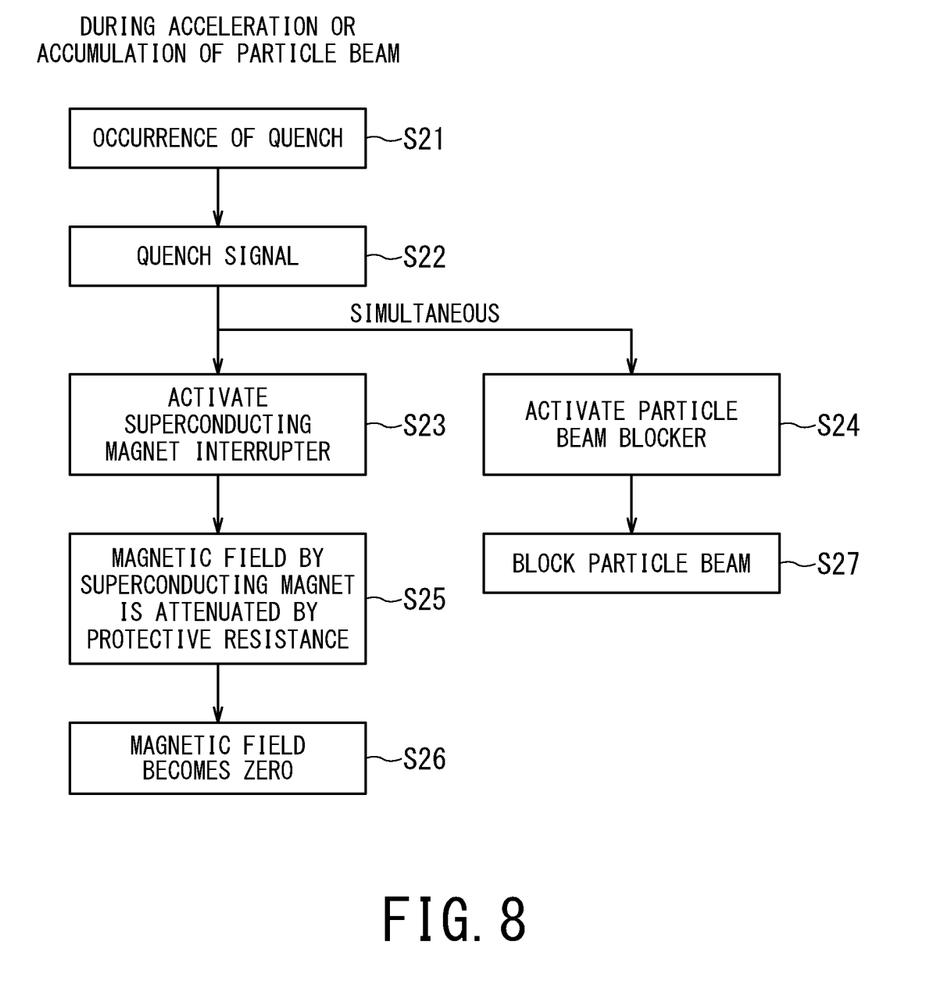
FIG. 8 is a flowchart illustrating a blocking procedure by the charged particle beam blocker and the superconducting electromagnet interrupter during acceleration or accumulation of the particle beam.

As shown in FIG. 8, the controller 30 performs the second blocking control. In the first step S21, during non-operation of the beam emitter 26 in the superconducting synchrotron 17, an abnormality such as quenching occurs in the superconducting electromagnet 32 of the superconducting electromagnet apparatus 31 constituting either or both the deflector 21 and the focusing/defocusing apparatus 22. For example, the abnormality such as quenching occurs at the time of: injection of the charged particle beam 1 by the beam injector 25; acceleration of the charged particle beam 1 by the high-frequency acceleration cavity 24; or accumulation of the accelerated charged particle beam 1.

In the next step S22, the quench detector (not shown) detects the abnormality such as quenching of the superconducting electromagnet 32 so as to output the quench signal, and then the controller 30 receives the quench signal from the quench detector.

In the next steps S23 and S24, the controller 30 simultaneously activates both the superconducting electromagnet interrupter 28 and the charged particle beam blocker 27 at the timing of receiving the quench signal from the quench detector.

In the next step S25 subsequent to the step S23, due to activation of the superconducting electromagnet interrupter 28, the magnetic field of the superconducting electromagnet 32 subjected to quenching or the like is attenuated by the protective resistance 35.

In the next step S26, interruption of the superconducting electromagnet 32 is completed at the timing when the magnetic field becomes zero.

In the next step S27 subsequent to the step S24, the charged particle beam 1 is blocked by activation of the charged particle beam blocker 27, and blocking of the charged particle beam 1 is completed.

The present embodiment has the above-described configuration and thus has the following effects.

When an abnormality such as quenching occurs in the superconducting electromagnet 32 of either or both the deflector 21 and the focusing/defocusing apparatus 22 in the superconducting synchrotron 17 as the particle beam accelerator 12, the controller changes the starting sequence of the charged particle beam blocker 27 and the superconducting electromagnet interrupter 28 depending on at least the operating state of the beam emitter 26. For example, when an abnormality such as quenching occurs in the superconducting electromagnet 32 during operation of the beam emitter 26, the controller 30 activates the charged particle beam blocker 27 so as to block the charged particle beam 1, and then activates the superconducting electromagnet interrupter 28 after completion of blocking the charged particle beam 1. Accordingly, the blocking of the charged particle beam 1 can be completed in the state where the current value of the superconducting electromagnet 32 subjected to quenching or the like does not decrease and is at an appropriate value. This can consequently reduce the risk of erroneous irradiation of the charged particle beam 1 emitted from the superconducting synchrotron 17 by the particle beam irradiator 14.

When an abnormality such as quenching occurs in the superconducting electromagnet 32 of the superconducting electromagnet apparatus 31 constituting either or both the deflector 21 and the focusing/defocusing apparatus 22 in a period during which the beam emitter 26 is not in operation but the beam injector 25 or the high-frequency acceleration cavity 24 is in operation, the controller 30 activates the superconducting electromagnet interrupter 28 simultaneously with the charged particle beam blocker 27. Hence, the superconducting electromagnet 32 subjected to quenching or the like is quickly interrupted, and thereby, rise in its coil temperature and generation of large voltage are suppressed. Thus, recooling time of the superconducting electromagnet 32 subjected to quenching or the like can be shortened, and consequently, the recovery time of this superconducting electromagnet 32 can be shortened.

The controller 30 of the present embodiment includes hardware resources such as a Central Processing Unit (CPU), a Read Only Memory (ROM), a Random Access Memory (RAM) and/or a Hard Disk Drive (HDD), and is configured as a computer in which information processing by software is achieved with the use of the hardware resources by causing the CPU to execute various programs. Further, the method for operating particle beam accelerator of the present embodiment is achieved by causing the computer to execute the various programs.

The controller 30 in the present embodiment includes a storage device such as the ROM and the RAM, an external storage device such as the HDD and a Solid State Drive (SSD), a display device such as a display panel, an input device such as a mouse and a keyboard, a communication interface, and a control device which has a highly integrated processor such as a Field Programmable Gate Array (FPGA), a Graphics Processing Unit (GPU), the CPU, and a special-purpose chip. The controller 30 can be achieved by hardware configuration with the use of the normal computer.

Note that each program executed in the controller 30 of the present embodiment is provided by being incorporated in a memory such as the ROM in advance. Additionally or alternatively, each program may be provided by being stored as a file of installable or executable format in a non-transitory computer-readable storage medium such as a CD-ROM, a CD-R, a memory card, a DVD, and a flexible disk (FD).

In addition, each program executed in the controller 30 may be stored on a computer connected to a network such as the Internet and be provided by being downloaded via a network. Further, the controller 30 can also be configured by interconnecting and combining separate modules, which independently exhibit respective functions of the components, via a network or a dedicated line.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A particle beam accelerator comprising:
an injection unit configured to inject a particle beam;
a guiding unit configured to guide the particle beam to a trajectory;
an acceleration unit configured to accelerate the particle beam circulating on the trajectory;
an emission unit configured to output the particle beam;
a particle beam blocking unit configured to block the particle beam on the trajectory; and
a control unit configured to control the injection unit, the guiding unit, the acceleration unit, the emission unit, and the particle beam blocking unit, wherein:
the guiding unit includes a superconducting electromagnet and a superconducting electromagnet interrupter configured to interrupt the superconducting electromagnet, and
the control unit is configured to change a starting sequence of the particle beam blocking unit and the superconducting electromagnet interrupter depending on at least an operating state of the emission unit, when an abnormality occurs in the superconducting electromagnet.

2. The particle beam accelerator according to claim 1, wherein:
the control unit is configured to activate the superconducting electromagnet interrupter after completion of blocking the particle beam by activating the particle beam blocking unit, when an abnormality occurs in the superconducting electromagnet during operation of the emission unit; and
the control unit is further configured to activate the superconducting electromagnet interrupter simultaneously with the particle beam blocking unit, when an abnormality occurs in the superconducting electromagnet during non-operation of the emission unit.

3. A method for operating a particle beam accelerator that comprises:
an injection unit configured to inject a particle beam;
a guiding unit configured to guide the particle beam to a trajectory;
an acceleration unit configured to accelerate the particle beam circulating on the trajectory;
an emission unit configured to output the particle beam; and
a particle beam blocking unit configured to block the particle beam on the trajectory, wherein:
the guiding unit includes a superconducting electromagnet and a superconducting electromagnet interrupter configured to interrupt the superconducting electromagnet, and
a starting sequence of the particle beam blocking unit and the superconducting electromagnet interrupter is changed depending on at least an operating state of the emission unit, when an abnormality occurs in the superconducting electromagnet.

4. A particle beam therapy apparatus comprising:
the particle beam accelerator according to claim 1; and
a particle beam irradiator configured to irradiate a lesion site of a patient with the particle beam accelerated by the particle beam accelerator for treatment.

* * * * *